252-95 AU 166 EX
8/5/80 XR 4,216,105

United States Patent [19]
Davidson et al.

[11] 4,216,105
[45] Aug. 5, 1980

[54] COMPOSITIONS FOR THE OPTICAL WHITENING OF ORGANIC MATERIALS AND USE THEREOF

[75] Inventors: Hugh Davidson, Castleford; Keith T. Johnson, Pontefract; Brian E. Leggeter, Wakefield; Anthony J. Moore, Leeds, all of England

[73] Assignee: Hickson & Welch Limited, Castleford, England

[21] Appl. No.: 965,048

[22] Filed: Nov. 30, 1978

Related U.S. Application Data

[60] Continuation of Ser. No. 797,383, May 16, 1977, abandoned, which is a division of Ser. No. 636,089, Nov. 28, 1975, Pat. No. 4,093,645, which is a division of Ser. No. 382,168, Jul. 24, 1973, Pat. No. 3,940,437.

[30] Foreign Application Priority Data

Jul. 26, 1972 [GB] United Kingdom ............... 35033/72

[51] Int. Cl.$^2$ ........................... C11D 3/42; C11D 9/44

[52] U.S. Cl. .................... 252/174.19; 8/648; 252/95; 252/99; 252/301.21; 260/505 R; 585/25

[58] Field of Search ............. 252/89 R, 89 B, 301.21, 252/95, 99, 174.19; 8/1 W; 260/505 R, 505 C

[56] References Cited

U.S. PATENT DOCUMENTS

| | | | |
|---|---|---|---|
| 3,627,758 | 12/1971 | Weber et al. | 252/95 X |
| 3,984,399 | 10/1976 | Weber et al. | 8/1 W |
| 4,013,713 | 3/1977 | Weber et al. | 260/505 R |

*Primary Examiner*—Mayer Weinblatt
*Attorney, Agent, or Firm*—Bacon & Thomas

[57] ABSTRACT

Compounds of the general formula R—CH=CH—W—CH=CH—R$^1$ are described in which R and R$^1$ are independently phenyl, diphenyl, naphthyl, indyl, tetrahydronaphthyl or acenaphthenyl and W is divalent phenyl, diphenyl, naphthyl, tetrahydronaphthyl or acenaphthenyl group, which groups may be substituted, the compounds containing at least one non-aromatic ring. Such compounds are useful as optical whitening agents, for example in textile material or paper.

11 Claims, No Drawings

COMPOSITIONS FOR THE OPTICAL WHITENING OF ORGANIC MATERIALS AND USE THEREOF

This is a continuation of application Ser. No. 797,383, filed May 16, 1977 now abandoned, which is in turn a division of application Ser. No. 636,089, filed Nov. 28, 1975, now U.S. Pat. No. 4,093,645, which is in turn a division of application Ser. No. 382,168, filed July 24, 1973, now U.S. Pat. No. 3,940,437.

This invention is concerned with new chemical compounds and processes for their preparation. These new compounds serve as fluorescent whitening agents and may, for example, be of use in the optical whitening and/or brightening of a wide variety of organic materials e.g. natural and synthetic yarns and fibres and the like. The compounds of the present invention are also potentially useful in the whitening and/or brightening of synthetic resin sheets and the like.

Optical whitening agents have in recent years found extensive use in the treatment of textile yarns and fibres, both in their preparation and during washing, and are designed in general to counteract the yellow or off-white colour which white textiles may develop. Such optical whitening agents also tend to improve coloured textiles as they impart a general brightness to them.

The present invention is based upon the discovery of certain compounds which have advantageous properties in the whitening and/or brightening of textile fibres or paper.

According to the present invention there are provided compounds of the general formula:

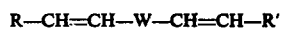

R—CH=CH—W—CH=CH—R'   I wherein R and R', which may be the same or different, each represents a group of the formula:

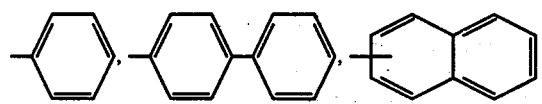

I(a)      I(b)      I(c)

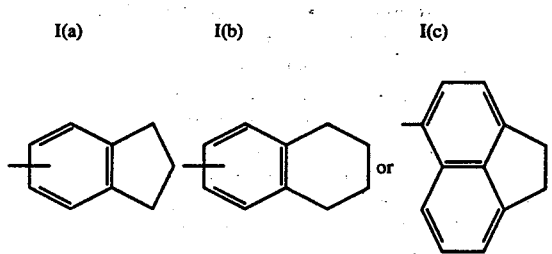

(I(d)      I(e)      I(f)

and W represents a group of the formula:

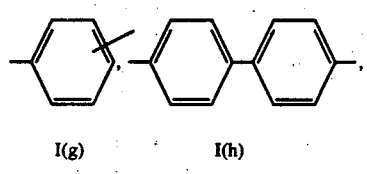

I(g)      I(h)

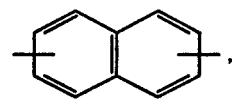

I(j)

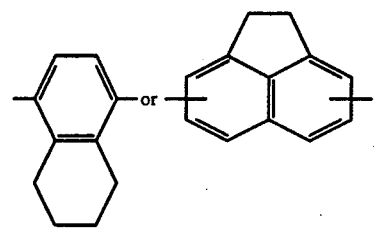

I(k)      I(l).

which group may be unsubstituted or substituted by one or more non-chromophoric substituents; said compounds of formula I containing at least one non-aromatic ring. In the compounds of formula I according to the invention, R and R' are conveniently the same group.

The compounds of formula I may exist in either the cis, cis-, trans, trans- or cis,trans- forms with respect to the ethylenic double bonds. It will be appreciated that all such forms of the compounds of formula I are within the scope of the present invention.

The fluorescent compounds according to the invention have especially advantageous properties in the whitening and/or brightening of textile yarns and fibres, in particular synthetic textile fibres (e.g. polyester, cellulosic and polyamide fibres). The compounds of the inventions are additionally useful as intermediates in the preparation of other compounds in accordance with the invention.

The compounds according to the present invention may also, if desired, be incorporated into synthetic melts e.g. of polyester resin which may subsequently be formed into textile yarns and fibres or other shaped articles such as, for example, synthetic resin sheets and films. Where for example textile yarns and fibres are to be formed, the compounds according to the invention may be incorporated into a synthetic resin melt e.g. a polyester resin melt, and the melt then extruded to form yarns or fibres.

The compounds of general formula I as hereinbefore defined which have been tested have exhibited a strong fluorescence both in solution and in the finely divided state, and moreover have shown a high heat resistance, fastness to light and bleach resistance.

The compounds which possess solubilising groups such as referred to below have been found to be particularly useful in low temperature washing applications, but have also a great effectiveness at higher temperatures. They thus have advantageous versatility in washing operations.

The water insoluble compounds of general formula I are, in general, useful for application to synthetic materials either in the melt or by exhaust treatment, dyeing with so-called carriers or by pad-bake application. Polyesters, in particular, are in general susceptible to such treatment, but other polymeric substrates may also be employed.

Compounds of general formula I which possess solubilising groups e.g. sulphonic or methylsulphonic acid groups, are especially suitable for application to cellulosic and polyamide fibres and may, for example, be used in an acid, neutral or detergent bath, as well as in a bleach containing bath.

In the compounds of formula I any non-chromophoric substituent present may for example be a sulphonic acid group which may if desired be functionally modified, a sulphone group, a carboxylic acid group which may if desired be functionally modified, or a cyano, hydroxyl, alkoxy (e.g. a $C_{1-6}$ alkoxy group, such as methoxy), alkyl (e.g. a $C_{1-6}$ alkyl group, such as methyl, which may be substituted by for example a sulphonic acid group) or oxadiazolyl (e.g. a 1,2,4-oxadiazolyl group, which may be unsubstituted or substituted for example by a $C_{1-6}$ alkyl group or a phenyl group) or a halogen atom (e.g. chlorine or bromine). The functionally modified sulphonic acid and carboxylic acid groups include for example the esters (e.g. $C_{1-6}$ alkyl esters), amides (e.g. N-alkyl amides in which the alkyl group has 1-6 carbon atoms) and halides (e.g. chlorides) thereof.

Such substituents will generally be present on the R and/or R' groups, but they may also be present on the W group.

Compounds of formula I which are generally preferred on account of their optical whitening properties are those which possess a 1,2,3,4-tetrahydronaphthalene residue, i.e. compounds in which R or R' (and conveniently both R and R') is a group of the formula I(e) or in which W is a group of the formula I(k). It is also generally preferred that the compounds of formula I should possess one or more substituents such as referred to above, particularly alkoxy groups or solubilising groups such as sulphonic or methylsulphonic acid groups.

Specific compounds of formula I which are preferred on account of their particularly advantageous optical whitening properties are:

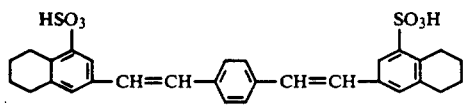

or a salt thereof;

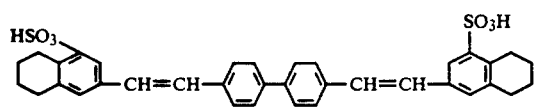

or a salt thereof;

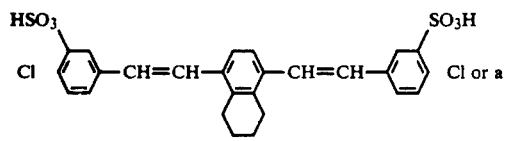

salt thereof; or

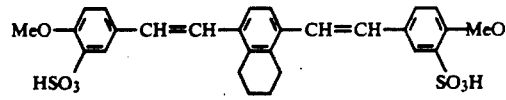

or a salt thereof.

Compounds possessing acid groups such as referred to above are capable of forming salts, and these salts are also within the scope of the invention.

The compounds according to the present invention may be prepared by any convenient process, but are advantageously prepared by the following process, which process constitutes a further feature of the present invention: reacting a compound of the formula:

$$Z—W—Z \quad\quad II$$

(wherein W is as hereinbefore defined and Z represents the group:

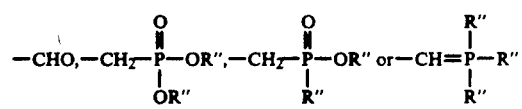

in which R" represents a substituted or unsubstituted alkyl, cycloalkyl or aryl group with a compound(s), of formula(e):

$$R—Z' \quad\quad III$$

and/or $$R'—Z' \quad\quad IV$$

(wherein R and R' are as hereinbefore defined and Z' is as defined for Z with the proviso that Z and Z' are different and one of Z and Z' represents the group —CHO).

Where it is desired to prepare a compound of formula I wherein R and R' represent the same groups, it is advantageous to use about 2 moles of the compound of formula III (or formula IV) per mole of the compound of formula II. Where it is desired to prepare a compound of formula I wherein R and R' are different, however, it is advantageous to use about 1 mole of the compound of formula III per mole of the compound of formula II as well as about 1 mole of the compound of formula IV per mole of the compound of formula II.

In the phosphorus containing compounds of formulae II and/or III and/or IV, where the group R" is bonded to oxygen said group is preferably a $C_{1-6}$ alkyl (e.g. methyl) group and where the group R" is bonded directly to phosphorus said group is preferably an aryl group, e.g. a phenyl group.

The reaction may, for example, be effected in the presence of a strongly basic alkali metal compound (e.g. sodium or potassium hydroxide) and advantageously also in the presence of a strongly polar solvent which is preferably hydrophilic (e.g. dimethylformamide). Where the strongly basic alkali metal compound used is an alkali metal hydroxide, water may additionally be present in an amount of up to 25% by weight of the hydroxide.

The reaction may be performed at any suitable temperature up to reflux, e.g. from 20°-65° C.

The phosphorus containing compounds of formulae II and/or III and/or IV may, for example, be obtained by reacting a halomethyl compound, preferably a chloromethyl compound of the formula:

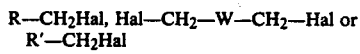

(wherein R, W and R' are as hereinbefore defined and Hal represents a halogen atom, preferably a chlorine atom) with a phosphorus compound of the formula:

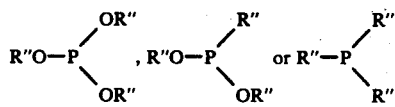

(wherein R" is as hereinbefore defined).

As stated above, where the group R" is bonded to oxygen said group is preferably a $C_{1-6}$ alkyl group and where the group R" is bonded directly to phosphorus said group is preferably an aryl group e.g. a phenyl group.

Compounds of formula I which are symmetrical (i.e. compounds wherein R and R' are the same and W is a diphenyl group of the formula I(g)) may also be prepared in accordance with the present invention by reduction of a diazonium salt of the formula

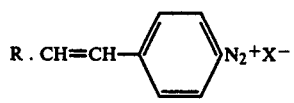

where R is as defined above and X is an anion (e.g. chloride). The reduction may be effected with cuprous ammonium hydroxide (which is desirably freshly prepared) in an aqueous medium at a low temperature (e.g. 0°-10° C.).

The non-chromophoric substituents which may be present on the groups R,R' and W of compounds of formula I are conveniently present on the corresponding groups of the starting materials from which the compound of formula I is prepared. Alternatively, such substituents may be introduced by conventional techniques into a compound of formula I subsequent to its preparation. For example, a halo (e.g. chloro) sulphonyl group may be introduced into an aromatic ring in the groups R and/or R' of a compound of formula I by reaction with thionyl halide (e.g. in a polar reaction medium at 20° C. or below).

Compounds of formula I possessing a sulphonamide substituent may be prepared by reacting a corresponding halosulphonyl (e.g. chlorosulphonyl) compound with a primary or secondary amine or ammonia (e.g. a monoalkylamine) or an ammonium salt. Reaction with an amine may for example be effected in the presence of a hydrocarbon solvent (e.g. toluene) at any suitable temperature up to reflux.

For the purpose of treating previously-formed textile yarns and fibres in general, the compounds according to the invention may be incorporated into compositions comprising at least one compound of formula I together with a solid or liquid carrier. Such compositions may, for example, be adapted for use in the washing of natural and synthetic yarns and fibres and can take the form of solutions, suspensions and dispersions of compounds of formula I in appropriate liquid carriers such as water, sulpholane, dimethylformamide and dimethylsulphoxide. When dispersions are used, they conveniently include dispersing agents such as, for example, alkyl naphthalene sulphenates. Aqueous compositions may, if desired, also contain, for example, synthetic detergents, soaps or surface-active agents. Alternatively the compositions may be in solid form and comprise at least one compound according to the invention together with a solid synthetic detergent or soap as carrier. The compounds of formula I may be employed in the manufacture of synthetic yarns and fibres e.g. by addition to compositions from which the fibres are prepared by spinning or extrusion.

The compounds of the invention may also be used, as indicated above, in whitening and/or brightening paper. This effect may be obtained either by including the compound of formula I (preferably a water soluble compound) in the pulp from which the paper is to be made, or by treating paper with a composition containing a compound of formula I (e.g. a sizing composition containing an adhesive starch or alginate).

The following examples, in which all parts are by weight and all temperatures are in °C., are given by way of illustration only:

EXAMPLE 1

A solution of 3.92 parts of 4,4'-bis(dimethoxyphosphonomethyl)-diphenyl and 6.9 parts of the sodium salt of 6-formyl-1,2,3,4-tetrahydronaphthalene-8-sulphonic acid (containing 76% pure sodium salt) in 75 parts of dimethyl formamide was stirred while 5 parts of powdered potassium hydroxide were added. The temperature was maintained at 20°-25° for 2 hours, raised slowly to 45° and further maintained at this temperature for 30 minutes. The reaction mixture was then diluted with 200 parts of water, strongly acidified with hydrochloric acid, boiled, cooled and the solid collected. The cream coloured product was dried at 50° to afford 6 parts of a product of formula:

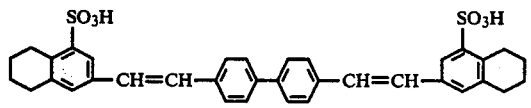

which dissolved in water in the presence of sodium carbonate to give an almost colourless solution with a strong violet-blue fluorescence.

Analysis of dibutylamine salt

| Calculated for $C_{36}H_{34}O_6S_2 \cdot 2C_8H_{19}N$ | C 70.6 | H 8.1 |
|---|---|---|
| | N 3.2 | S 7.2 |
| Found | C 70.5 | H 8.0 |
| | N 3.1 | S 7.5 |

The 4,4'-bis(dimethoxyphosphonomethyl)diphenyl used as starting material may be prepared in the following manner:

A mixture of 186 parts of trimethyl phosphite and 130 parts of 4,4'-bis-chloromethyldiphenyl was refluxed for 8 hours and then the excess of trimethyl phosphite distilled off under vacuum. The clear colourless residual solution was diluted with 200 parts of toluene and allowed to crystallize. The solid product was collected, washed with a little toluene to afford 80 parts of bis(- dimethoxyphosphonomethyl)-diphenyl, m.p.t. 131°-2° C.

EXAMPLE 2

16 parts of 6-formyl-1,2,3,4-tetrahydronaphthalene and 19.6 parts of 4,4'-bis(dimethoxyphosphonomethyl)-diphenyl in 100 parts of dimethylformamide were added to a suspension of 25 parts of potassium hydroxide in 100 parts of dimethylformamide at 45° C. over a period of 40 minutes. The mixture was heated to 65° for 30 minutes, cooled and poured into 750 parts of water. The product was filtered off and washed with water and methanol. Recrystallisation from dimethylformamide yielded 15 parts of pale yellow solid, m.p. 208°-210°., which imparted a vivid violet-blue fluorescence to its solutions in methanol.

Formula of product:

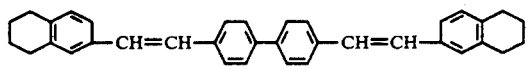

Analysis

| Calculated for $C_{36}H_{34}$ | C 92.7 | H 7.3 |
|---|---|---|
| Found | C 93.0 | H 7.0 |

The 6-formyl-1,2,3,4-tetrahydronaphthalene $b_{0.5}$ 110° (Semicarbazone, m.pt. 221°) can be obtained by treatment of 1,2,3,4-tetrahydronaphthalene with dichloromethyl butyl ether according to the method described by Rieche, Gross and Höft, Chemische Berichte, 93, 88 (1960). An alternative synthesis can be accomplished by chloromethylation of tetrahydronaphthalene and conversion of the resultant product to an aldehyde.

Sulphonation of 6-formyl-1,2,3,4-tetrahydronaphthalene with oleum containing 66% $SO_3$ afforded the 6-formyl-1,2,3,4-tetrahydronaphthalene-8-sulphonic acid used in Example 1.

EXAMPLE 3

Using an identical procedure to Example 2 but substituting 23.9 parts 6-bromo-1,2,3,4-tetrahydronaphthaldehyde for the 6-formyl-1,2,3,4-tetrahydronaphthalene, 9.1 parts of a product of formula:

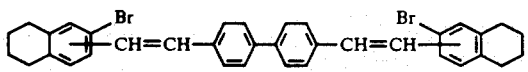

was obtained, m.pt. 212°-215°.

Analysis

| Calculated for $C_{36}H_{32}Br_2$ | C 69.3 | H 5.1 | Br 25.6 |
|---|---|---|---|
| Found | C 69.5 | H 4.9 | Br 25.7 |

The 6-bromo-1,2,3,4-tetrahydronaphthaldehyde was obtained by the treatment of 6-bromo-1,2,3,4-tetrahydronaphthalene according to the method of Rieche, Gross and Höft referred to in Example 2.

EXAMPLE 4

2 parts of the product of Example 1 slurried in 50 parts of dimethylformamide was treated at 0°-5° C. with 1.5 parts of thionyl chloride and the mixture slowly allowed to rise to room temperature over a period of 3 hours. The excess of thionyl chloride was destroyed by pouring the reaction mixture onto 200 parts of ice and the solid material was collected, washed with water and extracted with chloroform. The dried chloroform solution was distilled to yield 1.4 parts of a compound of the formula:

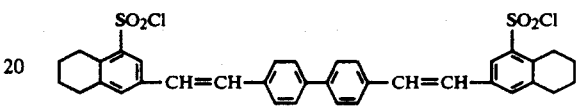

After recrystallization from benzene 1.0 parts of pale yellow solid were obtained. M.pt. above 270°.

Analysis

| Calculated for $C_{36}H_{32}Cl_2O_4S_2$ | C 65.2 | H 4.8 | Cl 10.7 |
|---|---|---|---|
| | S 9.7 | | |
| Found | C 64.9 | H 4.6 | Cl 10.8 |
| | S 9.8 | | |

EXAMPLE 5

0.7 parts of the product of Example 4 and 4 parts of n-butylamine were slurried in 100 parts of toluene and refluxed for 6 hours. The toluene was removed by steam distillation and the solid collected washed with water and methanol. After recrystallization from toluene the cream coloured solid melted at 238°-240° C.

Formula of product:

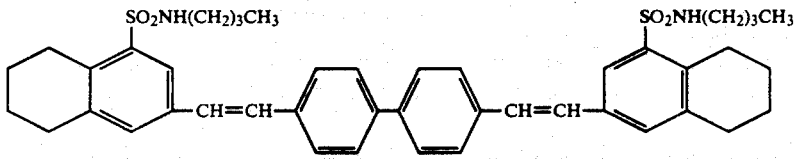

Analysis

| Calculated for $C_{44}H_{52}N_2O_4S_2$ | C 71.7 | H 7.1 | N 3.8 | S 8.7 |
|---|---|---|---|---|
| Found | C 71.4 | H 7.2 | N 4.2 | S 8.5 |

EXAMPLE 6

14 parts of 6(4-amino-2-sulphostyryl)-1,2,3,4-tetrahydronaphthalene (72% pure) was dissolved in 300 parts of hot water by the addition of 1.2 parts of sodium hydroxide. The solution was cooled to 5°, acidified with 8 parts of hydrochloric acid and diazotized by the addition of 2.1 parts of sodium nitrite. After completion of the diazotization the excess of sodium nitrite was destroyed with sulphamic acid. The diazonium salt was filtered off, washed with water and reslurried with 150 parts of water. 15 parts of cupric sulphate pentahydrate were dissolved in 120 parts of water and 18 parts of concentrated ammonium hydroxide added. This solution was reduced by the cautious addition of a solution of 6.8 parts of hydroxylamine hydrochloride and 5.3 parts of potassium hydroxide in 75 parts of water. The diazonium slurry was added to this reduced solution in portions over a period of 15 minutes while the temperature was maintained at 5°. After stirring for 1 hour, the solid product was filtered off and refluxed with 10 parts of stannous chloride in aqueous hydrochloric acid and enough ethanol to give a solution for 1 hour. The ethanol was distilled off and the solid material filtered off and washed with boiling water. The residual product was dissolved in hot aqueous ethanol and precipitated on cooling, 0.5 parts of a creamy yellow solid of the formula:

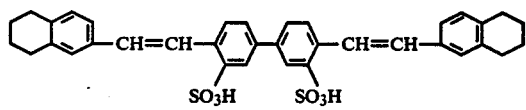

which displayed a vivid blue fluorescence in alkaline solution.

Analysis

| | | | |
|---|---|---|---|
| Calculated for $C_{36}H_{34}O_6S_2 \cdot 2H_2O$ | C 65.3 | H 5.7 | S 9.7 |
| Found | C 64.9 | H 5.5 | S 9.9 |

The 6(4-amino-2-sulphostyryl)-1,2,3,4-tetrahydronaphthalene may be prepared by the following route:

55 parts of 4-nitrotoluene-2-phenylsulphonate, 30 parts of 6-formyl-1,2,3,4-tetrahydronaphthalene and 2 parts of piperidine were heated at 135°–40° for 2 hours. The reaction mixture was cooled to 90° and 100 parts of acetic acid added. On heating to reflux a clear solution was obtained which precipitated 72 parts of 6(4-nitro-2-phenylsulphostyryl)-1,2,3,4-tetrahydronaphthalene on cooling, m.pt. 159°–62°. This compound was hydrolysed to the free sulphonic acid with sodium ethoxide and reduced with iron and acetic acid to the desired amine.

EXAMPLE 7

15 parts of 6-formyl-1,2,3,4-tetrahydronaphthalene and 16.1 parts of 1,4-bis(dimethoxyphosphonomethyl)-benzene in 150 parts of dimethylformamide were added in portions to 150 parts of dimethylformamide in which was suspended 25 parts of potassium hydroxide. The temperature was maintained at 40°–50° C. during the addition and then raised to 65° for 30 minutes. The reaction mixture was cooled and poured into cold water (500 parts). The precipitated solid was collected, washed with water and after recrystallisation from petroleum (100°–120° fraction), 9.1 parts of a pale lemon-yellow solid of m.pt. 193°–6° was obtained of formula:

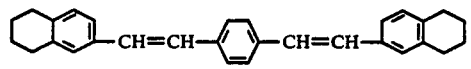

Analysis

| | | |
|---|---|---|
| Calculated for $C_{30}H_{30}$ | C 92.3 | H 7.7 |
| Found | C 92.3 | H 7.8 |

The same product was also obtained by the reaction of 25.4 parts of 6-(dimethoxyphosphonomethyl)-1,2,3,4-tetrahydronaphthalene and 6.7 parts of terephthaldehyde under similar conditions. 6-(Dimethoxyphosphonomethyl)-1,2,3,4-tetrahydronaphthalene, $b_{0.05}$ 146°–149°, was prepared from trimethylphosphite and 6-chloromethyl-1,2,3,4-tetrahydronaphthalene.

EXAMPLE 8

32.2 parts of 1,4-bis(dimethoxyphosphonmethyl)benzene and 52.4 parts 6-formyl-1,2,3,4-tetrahydronaphthalene-8-sulphonic acid (sodium salt) in 200 parts of dimethylformamide were treated with 45 parts of powdered potassium hydroxide. The exothermic reaction which ensues was controlled by external cooling so that the temperature did not exceed 30° and then the mixture was stirred for 24 hours at room temperature. The reaction mixture was quenched with 800 parts of water and 200 parts of sodium chloride added and stirred to dissolve. The solid which precipitated on stirring and cooling was filtered off, dissolved in 500 parts of hot water and reprecipitated by acidifying with concentrated hydrochloric acid. The solid was collected and recrystallized as sodium salt from 600 parts of boiling water made alkaline with sodium carbonate. A yield of 27 parts of a compound of formula:

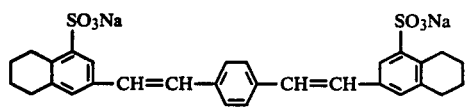

was thus prepared.

Analysis of dibutylamine salt

| | | | |
|---|---|---|---|
| Calculated for $C_{30}H_{30}O_6S_2 \cdot 2C_8H_{19}N$ | C 68.3 | H 8.4 | N 3.5 |
| | S 7.9 | | |
| Found | C 68.7 | H 8.2 | N 3.4 |
| | S 8.0 | | |

EXAMPLE 9

In an analogous manner to Example 8 a compound of formula:

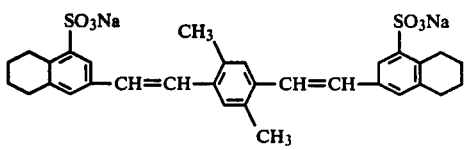

was prepared by substituting 35 parts of 1,4-bis(dimethoxyphosphonomethyl)-2,5-dimethylbenzene for the 32.2 parts of 1,4-bis(dimethoxyphosphonomethyl)benzene in that example.

Analysis of dibutylamine salt

| | | | |
|---|---|---|---|
| Calculated for $C_{32}H_{34}O_6S_2 \cdot 2C_8H_{19}N$ | C 68.9 | H 8.6 | N 3.3 |

```
                    S 7.7
         Found  C 69.1  H 8.9  N 3.6
                    S 7.4
```

EXAMPLE 10

18.8 parts of 5,8-bis(dimethoxyphosphonomethyl)-1,2,3,4-tetrahydronaphthalene and 10.6 parts of benzaldehyde in 150 parts of dimethylformamide were added in portions to a suspension of 25 parts of potassium hydroxide in 100 parts of dimethylformamide over a period of 40 minutes while the temperature was maintained at 40°–50°. The reaction mixture was stirred at 65° for 30 minutes, cooled well and poured into 500 parts of cold water. The precipitated solid was collected, well washed with water and methanol to yield 13 parts of a pale yellow solid, m.pt. 159°–161°, of formula:

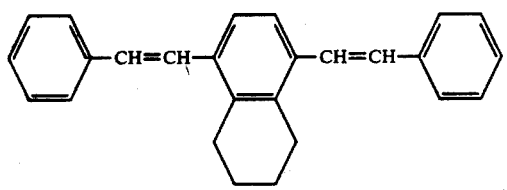

Analysis

| Calculated for $C_{26}H_{24}$ | C 92.9 | H 7.1 |
|---|---|---|
| Found | C 92.6 | H 7.3 |

The 5,8-bis(dimethoxyphosphonomethyl)-1,2,3,4-tetrahydronaphthalene used as starting material was prepared by the following route:

A mixture of 200 parts of trimethylphosphite and 76.3 parts of 5,8-bis-chloromethyl-1,2,3,4-tetrahydronaphthalene was refluxed for 12 hours and the excess of trimethyl phosphite distilled off. The residue was cooled and washed with petroleum ether, dissolved in hot toluene and the product reprecipitated with petroleum ether. The crystallized solid was washed with petrol and collected to afford 130 parts of 5,8-bis(dimethoxyphosphonomethyl)-1,2,3,4-tetrahydronaphthalene, m.pt. 88°–90°.

EXAMPLES 11, 12, 13 and 14

The following compounds of general formula:

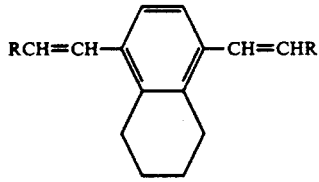

were prepared by substituting the appropriate aldehyde, RCHO for benzaldehyde in the procedure of Example 10

| Example | R | M.pt. | Colour |
|---|---|---|---|
| 11 | ![1-methylnaphthyl] | 224°–6° | Bright yellow |
| 12 | ![4-CO2CH3-phenyl] | 235° | Pale yellow |
| 13 | ![4-CN-phenyl] | 254°–6° | Bright yellow |
| 14 | ![oxadiazole-diphenyl] | 257° | Canary yellow |

EXAMPLE 11

Analysis

| Calculated for $C_{34}H_{28}$ | C 93.6 | H 6.4 |
|---|---|---|
| Found | C 93.8 | H 6.5 |

EXAMPLE 12

Analysis

| Calculated for $C_{30}H_{28}O_4$ | C 79.6 | H 6.2 |
|---|---|---|
| Found | C 79.6 | H 6.4 |

EXAMPLE 13

Analysis

| Calculated for $C_{28}H_{22}N_2$ | C 87.0 | H 5.7 | N 7.3 |
|---|---|---|---|
| Found | C 87.2 | H 5.6 | N 7.0 |

EXAMPLE 14

Analysis

| Calculated for $C_{42}H_{32}N_4O_2$ | C 80.8 | H 5.1 | N 9.0 |
|---|---|---|---|
| Found | C 80.4 | H 5.4 | N 8.8 |

EXAMPLE 15

Replacing the benzaldehyde in Example 10 by 20.8 parts of the sodium salt of o-sulphobenzaldehyde, a final reaction mixture was obtained which was poured into 750 parts of water and the product precipitated by the addition of 150 parts of sodium chloride. This product was redissolved in hot water and converted to the free acid by boiling with hydrochloric acid. It was filtered off and recrystallized as sodium salt from 300 parts of boiling water made alkaline with sodium carbonate. The yield was 13 parts of a bright lemon solid of formula:

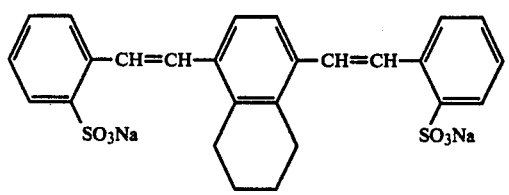

Analysis of dibutylamine salt

| | | | |
|---|---|---|---|
| Calculated for $C_{26}H_{24}O_6S_2 \cdot 2C_8H_{19}N$ | C 66.8 | H 8.2 | N 3.7 |
| | S 8.5 | | |
| Found | C 66.5 | H 8.2 | N 3.6 |
| | S 8.5 | | |

EXAMPLES 16, 17, 18, 19, 20, 21 AND 22

In experiments analogous to those of Example 15 the following sulphonic acid derivatives (having the general formula shown in Example 11) were prepared:

| Example | R | Colour of powder |
|---|---|---|
| 16 | ![4-SO3Na phenyl] | Pale yellow |
| 17 | ![3-SO3Na phenyl] | Pale yellow |
| 18 | ![4-CH3, 3-SO3Na phenyl] | Creamy white |
| 19 | ![4-SO3Na, 3-Cl phenyl] | Pale yellow |
| 20 | ![2-SO3Na, 3-Cl phenyl] | Primrose yellow |
| 21 | ![2-SO3Na, 3-OCH3 phenyl] | Pale yellow |
| 22 | ![SO3Na-tetrahydronaphthyl with methyl] | Yellow |

EXAMPLE 16

Analysis of dibutylamine salt

Calculated for $C_{26}H_{24}O_6S_2 \cdot 2C_8H_{19}N$  C 66.8  H 8.2  N 3.7

S 8.5
Found C 66.7  H 8.1  N 3.6
S 8.5

EXAMPLE 17

Analysis of dibutylamine salt

| | | | |
|---|---|---|---|
| Calculated for $C_{26}H_{24}O_6S_2 \cdot 2C_8H_{19}N$ | C 66.8 | H 8.2 | N 3.7 |
| | S 8.5 | | |
| Found | C 67.1 | H 8.1 | N 3.6 |
| | S 8.5 | | |

EXAMPLE 18

Analysis of dibutylamine salt

| | | | |
|---|---|---|---|
| Calculated for $C_{78}H_{28}O_6S_2 \cdot 2C_8H_{19}N$ | C 67.5 | H 8.4 | N 3.6 |
| | S 8.2 | | |
| Found | C 67.4 | H 8.3 | N 3.5 |
| | S 8.2 | | |

EXAMPLE 19

Analysis of dibutylamine salt

| | | | |
|---|---|---|---|
| Calculated for $C_{26}H_{22}Cl_2O_6S_2 \cdot 2C_8H_{19}N$ | C 61.2 | H 7.3 | Cl 8.6 |
| | N 3.4 | S 7.8 | |
| Found | C 61.2 | H 7.4 | Cl 8.6 |
| | N 3.5 | S 7.5 | |

EXAMPLE 20

Analysis of dibutylamine salt

| | | | |
|---|---|---|---|
| Calculated for $C_{26}H_{22}Cl_2O_6S_2 \cdot 2C_8H_{19}N$ | C 61.2 | H 7.3 | Cl 8.6 |
| | N 3.4 | S 7.8 | |
| Found | C 61.0 | H 7.6 | Cl 8.6 |
| | N 3.5 | S 7.5 | |

EXAMPLE 21

Analysis of dibutylamine salt

| | | | |
|---|---|---|---|
| Calculated for $C_{28}H_{28}O_8S_2 \cdot 2C_8H_{19}N$ | C 64.9 | H 8.1 | N 3.4 |
| | S 7.9 | | |
| Found | C 64.6 | H 8.4 | N 3.2 |
| | S 7.7 | | |

EXAMPLE 22

Analysis of dibutylamine salt

| | | | |
|---|---|---|---|
| Calculated for $C_{34}H_{36}O_6S_2 \cdot 2C_8H_{19}N$ | C 69.6 | H 8.6 | N 3.2 |
| | S 7.4 | | |
| Found | C 69.6 | H 8.8 | N 3.2 |
| | S 7.5 | | |

EXAMPLE 23

A compound of formula:

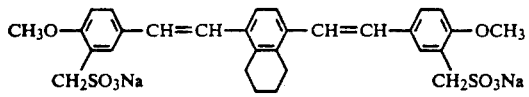

was prepared by the method of Example 15 using 3-sulphomethyl-p-anisaldehyde as the aldehyde reactant. It was isolated as a pale yellow powder recrystallized from aqueous ethanol.

Analysis of dibutylamine salt

| Calculated for $C_{30}H_{32}O_8S_2 \cdot 2C_8H_{19}N$ | C 65.6 | H 8.3 | N 3.3 |
|---|---|---|---|
| | S 7.6 | | |
| Found | C 65.3 | H 8.4 | N 3.4 |
| | S 7.6 | | |

The 3-sulphomethylanisaldehyde was prepared in the following manner:

13.6 parts of p-anisaldehyde, 6 parts of paraformaldehyde and 20 parts of zinc chloride were heated with 100 parts of concentrated hydrochloric acid at 70°–75° for 30 minutes. The mixture was poured into water and the solid collected, washed with water and dried. After recrystallizing from light petroleum 18.2 parts of 3-chloromethyl-4-methoxybenzaldehyde, m.pt. 54°, were obtained. This was dissolved in 80 parts of dioxan and refluxed with a solution of 30 parts of sodium sulphite heptahydrate in 80 parts of water for 1 hour. After removal of the insoluble material the resultant solution was concentrated to half its volume and 20 parts of the sodium salt of 4-methoxy-3-sulphomethylbenzaldehyde crystallised. (Analysis: calculated for $C_9H_9O_5\text{-SNa}\cdot 1\text{-}H_2O$ C 40.0, H 4.1, S 11.8, Na 8.5; Found: C 40.5, H 4.1, S 11.1, Na 8.5).

EXAMPLE 24

3.2 parts of 1,4-bis(dimethoxyphosphonomethyl)benzene, 2.5 parts of the sodium salt of 6-formyl-1,2,3,4-tetrahydronaphthalene-8-sulphonic acid and 2.4 parts of 4-methoxy-3-sulphomethylbenzaldehyde in 20 parts of dimethylformamide were treated with 1.5 parts of sodium methoxide and the temperature slowly raised to 45° for 5 hours. The reaction mixture was diluted with 100 parts of water and the product salted out by the addition of 20 parts of sodium chloride. There were thus obtained 5 parts of a light yellow solid which was a mixture, the major component of which had the formula:

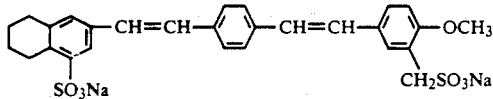

Analysis of dibutylamine salt

| Calculated for $C_{28}H_{28}O_7S_2 \cdot 2C_8H_{19}N$ | C 66.2 | H 8.3 | N 3.5 |
|---|---|---|---|
| | S 8.0 | | |
| Found | C 65.9 | H 8.1 | N 3.5 |
| | S 7.9 | | |

EXAMPLE 25

26.2 parts of 6-formyl-1,2,3,4-tetrahydronaphthalene-8-sulphonic acid (sodium salt) and 35 parts 1,4-xylylene-bis(triphenylphosphoniumchloride) in 500 parts of methanol were treated with 1.5 parts of lithium ethoxide. The mixture was refluxed for 5 hours and then concentrated under vacuum to 100 parts. The solid precipitated was collected, washed with methanol and dried. 12 parts of the compound of formula:

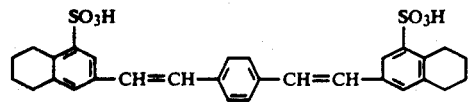

were obtained.

Analysis of dibutylamine salt

| Calculated for $C_{30}H_{30}O_6S_2 \cdot 2C_8H_{19}N$ | C 68.3 | H 8.4 | N 3.5 |
|---|---|---|---|
| | S 7.9 | | |
| Found | C 68.5 | H 8.1 | N 3.6 |
| | S 8.0 | | |

EXAMPLE 26

In a similar manner to Example 24 but using 1,4-bis(-dimethoxyphosphonomethyl)-3,5-dimethylbenzene the compound of formula:

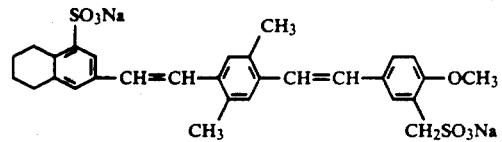

was obtained.

Analysis of dibutylamine salt

| Calculated for $C_{30}H_{32}O_7S_2 \cdot 2C_8H_{19}N$ | C 66.8 | H 8.5 | N 3.4 |
|---|---|---|---|
| | S 7.7 | | |
| Found | C 67.2 | H 8.3 | N 3.4 |
| | S 8.1 | | |

EXAMPLE 27

The compound of formula:

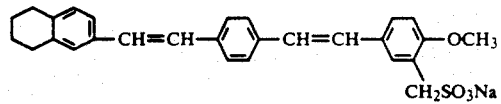

was obtained by replacing the 6-formyl-1,2,3,4-tetrahydronaphthalene-8-sulphonic acid in Example 24 by 6-formyl-1,2,3,4-tetrahydronaphthalene.

Analysis of dibutylamine salt

| Calculated for $C_{28}H_{28}O_4S \cdot C_8H_{19}N$ | C 73.3 | H 8.0 | N 2.4 |
|---|---|---|---|
| | S 5.4 | | |
| Found | C 73.0 | H 7.8 | N 2.3 |
| | S 5.2 | | |

EXAMPLE 28

13.1 parts of 6-formyl-1,2,3,4-tetrahydronaphthalene-8-sulphonic acid (sodium salt) and 15.1 parts of 4-(dimethoxyphosphonomethyl)-stilbene in 75 parts of dimethylformamide were treated with 5 parts of potassium hydroxide and allowed to stand for 60 hours at room temperature. The mixture was then poured into 400 parts of water and the product precipitated by the addition of 100 parts of sodium chloride. The crude product was recrystallized from 80% aqueous ethanol and a light yellow solid was obtained of formula:

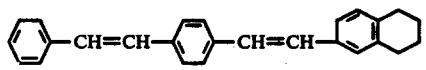

which imparted a vived violet-blue fluorescence to its alkaline solutions.

Analysis of dibutylamine salt

| Calculated for $C_{26}H_{24}O_3S \cdot C_8H_{19}N$ | C 74.9 | H 7.9 | N 2.6 |
|---|---|---|---|
|  | S 5.9 |  |  |
| Found | C 74.9 | H 7.8 | N 2.5 |
|  | S 5.8 |  |  |

The 4-(dimethoxyphosphonomethyl)-stilbene may be obtained from 4-bromomethylstilbene, itself prepared by the bromination of 4-methylstilbene with N-bromosuccinimide.

EXAMPLE 29

7 parts of bis(dimethoxyphosphonomethyl)acenaphthene and 8 parts of o-sulphobenzaldehyde were treated in 50 parts of dimethylformamide with a suspension of 8.7 parts of potassium hydroxide in 50 parts of dimethylformamide. The temperature was maintained at 45° for 1 hour, raised to 65° for 15 minutes and then the reaction mixture cooled wall and diluted with 400 parts of water. The product was salted out by the addition of 100 parts of sodium chloride, collected, washed with water and converted to the free acid by boiling with hydrochloric acid. It was filtered off, redissolved in water by the addition of soda ash and recrystallised to afford 2.5 parts of a compound of formula:

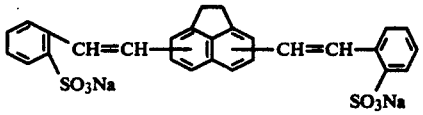

This compound exhibits a strong blue fluorescence in solution.

Analysis of dibutylamine salt

| Calculated for $C_{28}H_{22}O_6S_2 \cdot 2C_8H_{19}N$ | C 68.0 | H 7.7 | N 3.6 |
|---|---|---|---|
|  | S 8.2 |  |  |
| Found | C 68.2 | H 7.4 | N 3.5 |
|  | S 7.9 |  |  |

The bis(dimethoxyphosphonomethyl)acenaphthene may be prepared by the following route.

154 parts of acenaphthene, 350 parts of formaldehyde and 1,000 parts of concentrated hydrochloric acid were heated for 15 hours at 80°–90° while gaseous hydrogen chloride was continuously passed. The resultant non-aqueous layer was separated and washed by decantation with water. The semi-solid material was recrystallised from 500 parts of acetone, subsequently from dichloromethane and finally from toluene to afford a bis(-chloromethyl)acenaphthene of m.pt. 212°–3°.

| Analysis calculated | C 66.9 | H 4.8 | Cl 28.2 |
|---|---|---|---|
| found | C 66.4 | H 4.9 | Cl 27.6 |

10 parts of the bis(chloromethyl)acenaphthene were refluxed with 30 parts of trimethylphosphite for 10 hours and the excess of trimethylphosphite removed under reduced pressure. The product was precipitated by the addition of 50 parts of petrol and filtered off, washed with petrol and recrystallised from toluene to afford 10 parts of a bis(dimethoxyphosphonomethyl)acenaphthene of m.pt. 115°–7°.

| Analysis calculated | P 15.6 | $CH_3O$ | 31.2 |
|---|---|---|---|
| found | P 15.0 | $CH_3O$ | 30.4 |

EXAMPLE 30

A bleached cotton fabric was washed at a liquor to goods ratio of 40:1 for 30 minutes at 60° in a bath containing:

0.03 g./l. of the compound of Example 1, 8, 20 or 21.
1 g./l of active chlorine (Javelle water)
4 g./l of a washing powder of the following composition:
- 15% Dodecylbenzene sulphonate
- 10% Sodium laurylsulphonate
- 40% Sodium tripolyphosphate
- 25.75% Anhydrous sodium sulphate
- 71% Sodium metasilicate
- 2% Carboxymethylcellulose
- 0.25% EDTA (ethylenediaminetetraacetic acid)

After having been rinsed and dried, the fabric exhibited a strong brightening effect which showed good fastness to acids, chlorine and light.

Alternatively the brightener of Example 1, 8, 20 or 21 may be directly incorporated in the washing powder of the above composition. Strong brightening effects were also obtained when the fabric was washed at 20° for 30 minutes.

EXAMPLE 31

A bleached cotton fabric was washed at a liquor to goods ratio of 20:1 for 30 minutes at 60°–95° in a bath containing:

0.04 g./l of the compound of Example 1
4 g./l of a washing powder of the following composition:
- 40% Soap flakes
- 15% Sodium tripolyphosphate
- 8% Sodium perborate
- 1% Magnesium silicate
- 11% Sodium metasilicate nonahydrate
- 24.5% Sodium carbonate
- 0.5% Ethylenediaminetetraacetic acid The rinsed and dried cotton fabric displayed a strong brightening effect. Excellent brightening effects were also produced at lower temperatures.

EXAMPLE 32

A boiled cotton fabric was treated at a liquor to goods ratio of 40:1 for 1 hour at 25° in a bath containing:
- 0.1% (by weight of fibres) of the compound of Example 1 or 8
- 2 g./l of active chlorine, as Javelle water.

The fabric was then rinsed and subjected to an antichlor treatment and after drying exhibited a strong brightening effect.

EXAMPLE 33

An unbleached cotton fabric was treated at a liquor to goods ratio of 40:1 for 1–2 hours at 80°–90° in a bath containing:
- 0.1% (by weight of fibres) of the compound of Example 1 or 8
- 2 g./l Sodium chlorite
- 2 g./l Sodium nitrate
- 1 g./l Sodium pyrophosphate The pH of the bath was adjusted to 3.8–4.2 by the addition of formic acid, and after the treatment the fabric was rinsed and immersed in a bath containing:
- 1 g./l Sodium perborate
- 1 g/l Soap at 80° for 30 minutes.

The rinsed and dried fabric exhibited a brilliant whiteness.

EXAMPLE 34

Polyamide fibre fabric was treated at a liquor to goods ratio of 40:1 for 30–45 minutes at a temperature of 90°–100° in a bath, adjusted to pH 4 by addition of formic acid, containing:
- 0.1% (by weight of fibres) of the compound of Example 8
- 2 g./l Sodium chlorite
- 2 g./l Sodium nitrate
- 1 g./l Sodium pyrophosphate The rinsed fabric was given an anti-chlor treatment in a bath containing 2 g./l sodium metabisulphite for 15 minutes at 40°–50°. The resultant fabric after rinsing and drying displayed a very good brightening effect. Similar effects were obtained with polyester fibre fabrics.

EXAMPLE 35

Polyamide fibres were treated at a liquor to goods ratio of 40:1 at 60°–100° in a bath containing 0.1% (by weight of fibres) of the compound of Example 1, 8, 20 or 21. The bath was raised to the boil within 30 minutes and maintained at this temperature for a further 30 minutes. The rinsed and dried fibres exhibited a strong brightening effect of good fastness to light.

EXAMPLE 36

Bleached woollen fibre fabric was treated at a liquor to goods ratio of 40:1 for 1 hour in a bath containing 0.1% (by weight of fibres) of the compound of Example 15, 20 or 21 and 4 g./l of sodium dithionate. After rinsing and drying the fibres showed a good brightening effect which had a good light fastness. Similar results were obtainable if 5% acetic acid replaced the sodium dithionate.

EXAMPLE 37

Polyvinylchloride fibres were padded at room temperature with an aqueous dispersion which contained 0.5 g./l of the compound of Example 12 or 13 and the fabric was dried at 100° and then subjected to a heat treatment for 30 seconds at 190°. The resultant fabric showed a pronounced whitening effect.

EXAMPLE 38

Polyvinylchloride fibres were padded at 20° with an aqueous dispersion which contained 1 g./l of the compound of Example 5 and then dried at 70°. The dry material was heated at 100° for 3 minutes and a substantially improved whiteness was imparted to the fabric.

EXAMPLE 39

A fabric composed of cellulose acetate fibres was immersed at a liquor to goods ratio of 40:1 at 50° in an aqueous bath containing 0.15% (by weight of fibres) of a compound of Example 5. The temperature of the bath was then raised to 90°–95° and maintained at this temperature for 30–45 minutes. After rinsing and drying the fabric displayed a good whitening effect.

EXAMPLE 40

Paper pulp containing 100 parts of bleached cellulose was mixed with 2 parts of resin size in a pulping machine and after 15 minutes a solution of 0.2 parts of the compound of Example 1 in 20 parts of water was added. After a further 15 minutes, 3 parts of aluminium sulphate were added. After passing through a mixing vat the pulp was made into paper in the usual manner in a suitable machine. Paper of a high whiteness was produced.

EXAMPLE 41

Paper pulp containing 100 parts of bleached cellulose was mixed with 2 parts of resin size and after 15 minutes 3 parts of aluminium sulphate were added. The pulp was manufactured into a paper web on a paper making machine, and subjected to a superficial sizing in a size press with an adhesive starch or alginate containing 0.15 parts of the compound of Examples 1, 8, 20 or 21. A paper of very high whiteness was produced.

EXAMPLE 42

3.0 Parts of the sodium salt of indane-5-aldehyde-7-sulphonic acid (82% pure) and 1.96 parts of 4,4'-bis(dimethoxyphosphonomethyl)diphenyl in 10 parts of dimethyl formamide were added to a suspension of 25 parts of potassium hydroxide in 10 parts of dimethylformamide at 45° C. over a period of 40 minutes. The mixture was heated to 65° for 30 minutes, cooled and poured into 75 parts of water. After acidification with hydrochloric acid the product was collected and well washed with water. A pale yellow product of formula:

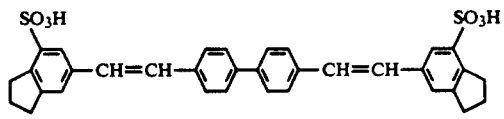

was obtained which dissolved in water in the presence of sodium carbonate to give an almost colourless solution with a strong violet blue fluorescence.

ANALYSIS

| | | | |
|---|---|---|---|
| Calculted for $C_{34}H_{30}O_6S_2 \cdot 2H_2O$ | C 64.4 | H 5.4 | S 10.1 |
| Found | C 63.9 | H 5.6 | S 9.8 |

Indane-5-aldehyde-7-sulphonic acid was prepared by treatment of indane-5-aldehyde with oleum containing 66% SO₃.

Indane-5-aldehyde, (anil m.pt. 85°–86°), may be obtained by chloromethylation of indane and conversion of the resultant product to an aldehyde.

We claim:

1. A composition for the optical whitening and brightening of organic materials, consisting essentially of an effective amount of a compound of the formula:

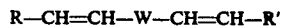

wherein R and R', which may be the same or different, each represents a group of the formula:

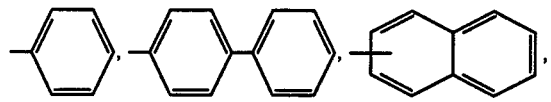

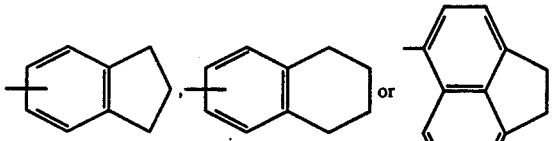

and W represents a group of the formula:

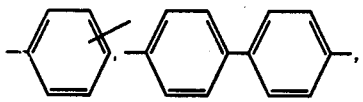

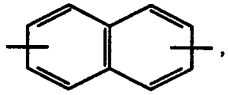

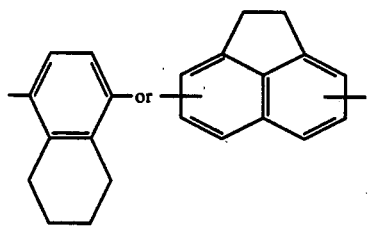

which groups may be unsubstituted or substituted by at least one non-chromophoric substituent selected from the group consisting of a sulphonic acid group, a carboxylic acid group, a sulfone group, cyano, hydroxyl, $C_{1-6}$ alkoxy, $C_{1-6}$ alkyl unsubstituted or substituted by a sulphonic acid group, oxadiazolyl unsubstituted or substituted by $C_{1-6}$ alkyl or phenyl, halogen and, when said substituent is a sulphonic acid or carboxylic acid group, an ester, amide, halide or salt thereof; said compound of formula I containing at least one of the groups I(d), I(e), I(f), I(k) and I(l), and a carrier therefor.

2. A composition as claimed in claim 1 wherein said compound is

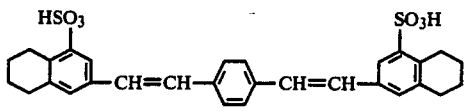

or a salt thereof;

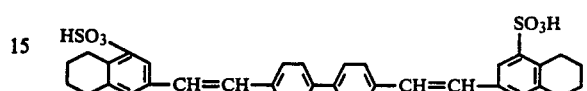

or a salt thereof;

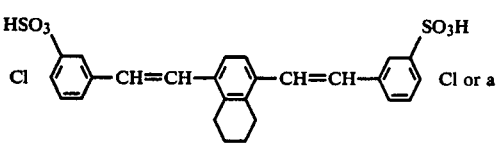

salt thereof; or

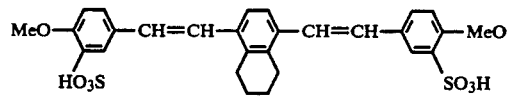

or a salt thereof.

3. A composition as claimed in claim 1 in solid form, the carrier being a solid synthetic detergent or soap.

4. A composition as claimed in claim 1 in which said carrier is a liquid selected from the group consisting of water, sulpholane, dimethylformamide and dimethylsulphoxide.

5. A composition as claimed in claim 1 in which said carrier is water containing a surface active agent.

6. A composition as claimed in claim 1 wherein in said compound W is a group of formula I(g), I(h), I(j) or I(k), and R and R' are independently groups of the formula I(a), (b), (c), (e) or (f).

7. A composition as claimed in claim 6 wherein in said compound at least one of R and R' is a group of the formula I(e) or W is a group of the formula I(k).

8. A composition as claimed in claim 6 wherein in said compound R and R' are the same.

9. A composition as claimed in claim 6 wherein in said compound at least one non-chromophoric substituent is present on at least one of R and R'.

10. A composition as claimed in claim 6 wherein said compound possesses a $C_{1-6}$ alkoxy, halo, sulphonic acid or sulphonic acid salt substituent.

11. A method of optical whitening and brightening of an organic material, comprising applying to said material an effective amount of a compound of the formula

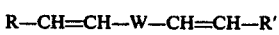

wherein R and R', which may be the same or different, each represents a group of the formula:

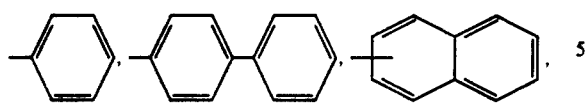

I(a)   I(b)   I(c)

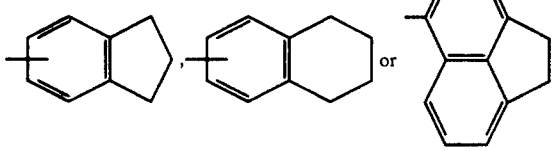

I(d)   I(e)   I(f)

and W represents a group of the formula:

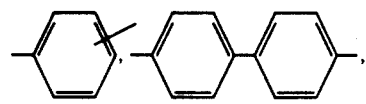

I(g)   I(h)

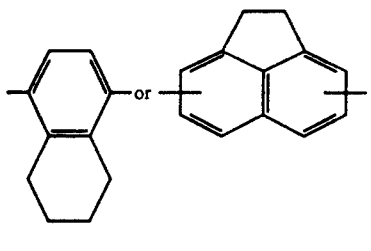

I(j)

I(k)   I(l).

which groups may be unsubstituted or substituted by at least one non-chromophoric substituent selected from the group consisting of a sulphonic acid group, a carboxylic acid group, a sulphone group, cyano, hydroxyl, $C_{1-6}$ alkoxy, $C_{1-6}$ alkyl unsubstituted or substituted by a sulphonic acid group, oxadiazolyl unsubstituted or substituted by $C_{1-6}$ alkyl or phenyl, halogen and, when said substituent is a sulphonic acid or carboxylic acid group, an ester, amide, halide or salt thereof; said compound of formula I containing at least one of the groups I(d), I(e), I(f), I(k) and I(l).

* * * * *